United States Patent [19]

Hulstrom et al.

[11] Patent Number: 4,779,980

[45] Date of Patent: Oct. 25, 1988

[54] ATMOSPHERIC OPTICAL CALIBRATION SYSTEM

[75] Inventors: Roland L. Hulstrom, Bloomfield; Theodore W. Cannon, Golden, both of Colo.

[73] Assignee: Midwest Research Institute, Kansas City, Mo.

[21] Appl. No.: 20,504

[22] Filed: Mar. 2, 1987

[51] Int. Cl.$^4$ ................................................ G01J 3/28
[52] U.S. Cl. ................................................ 356/218
[58] Field of Search ........................ 356/218, 221, 229

[56] References Cited

U.S. PATENT DOCUMENTS

| | | |
|---|---|---|
| 2,037,925 | 4/1936 | Rentschler . |
| 2,944,190 | 7/1960 | Ost . |
| 3,999,061 | 12/1976 | McLaughlin et al. . |
| 4,015,116 | 3/1977 | Bahm . |
| 4,168,124 | 9/1979 | Pizza . |
| 4,212,535 | 7/1980 | Sanders et al. . |
| 4,373,809 | 2/1983 | Gobrecht . |
| 4,511,250 | 4/1985 | Olsen ........................... 356/225 X |
| 4,560,279 | 12/1985 | Kouns ........................... 356/364 X |
| 4,609,288 | 9/1986 | Dodge ........................... 356/218 |

OTHER PUBLICATIONS

R. E. Bird and C. J. Riordan, Simple Solar Spectral Model for Direct and Diffuse Irradiance on Horizontal and Tilted Planes at the Earth's Surface for Cloudless Atmospheres, 1-86, 87-97.

C. R. Osterwald, Translation of Device Performance Measurements to Reference Conditions, 6-86, CP215-2713.

R. Perez and R. Stewart, Solar Irradiance Conversion Models, 6-30, CP215-2713.

Primary Examiner—R. A. Rosenberger
Assistant Examiner—S. McGowan
Attorney, Agent, or Firm—Ken Richardson; Terry Clausen

[57] ABSTRACT

An atmospheric optical calibration system is provided to compare actual atmospheric optical conditions to standard atmospheric optical conditions on the basis of aerosol optical depth, relative air mass, and diffuse horizontal skylight to global horizontal photon flux ratio. An indicator can show the extent to which the actual conditions vary from standard conditions. Aerosol scattering and absorption properties, diffuse horizontal skylight to global horizontal photon flux ratio, and precipitable water vapor determined on a real-time basis for optical and pressure measurements are also used to generate a computer spectral model and for correcting actual performance response of a photovoltaic device to standard atmospheric optical condition response on a real-time basis as the device is being tested in actual outdoor conditions.

22 Claims, 5 Drawing Sheets

ATMOSPHERIC OPTICAL CALIBRATION SYSTEM

CONTRACTUAL ORIGIN OF THE INVENTION

The United States Government has rights in this invention under Contract No. DE-AC02-83CH10093 between the U.S. Department of Energy and the Solar Energy Research Institute, a Division of Midwest Research Institute.

BACKGROUND OF THE INVENTION

1. Field of Invention

This invention relates generally to atmospheric optical and solar energy measuring systems and more specifically to a method and apparatus for measuring optical conditions of the atmosphere in real time, estimating spectral solar radiation, and comparing with standard conditions.

2. Description of the Prior Art

The sun, for practical purposes, provides an essentially constant source of solar energy. However, it is known that a variety of factors or parameters affect the amount and character of solar energy that reach any particular place on the surface of the earth. Thus, effective useable solar energy, such as for powering photovoltaic cells and similar uses, varies as a function of a variety of parameters, including relative position of the sun to the place on earth where the photovoltaic cell or other use is positioned, the atmospheric conditions, and the like.

More specifically, it has been shown that the performance characteristics of photovoltaic devices (e.g., short-circuit current, efficiency factor, open circuit voltage, and power output) vary as functions of atmospheric optical parameters and the spectral solar irradiance incident on the photovoltaic devices. Consequently, when photoelectric devices are tested in outdoor ambient conditions, the performance data will contain a certain amount of variability from one place to the next and from one time to the next.

For example, it is known that incident spectral solar irradiance conditions are quite variable because of such parameters as extraterrestrial solar irradiance characteristics, the optical transmittance properties of the intervening atmosphere, the slant path of the direct-beam sunlight through the atmosphere, and the reflectance properties of the ground as viewed by the photovoltaic device. In other words, the inherent temporal and spatial (geographical) variability of atmospheric optical conditions, along with variations in relative air mass, which is a function of location, time of day, and time of year, creates variables in the spectral solar irradiance incident on photovoltaic devices tested outdoors.

To compare quality and performance of various photovoltaic devices, it is necessary to have some standard reference conditions against which, or in which, all photovoltaic devices can be tested or to which individual test results can be correlated. One method that persons who work in the photovoltaic field have used to correct outdoor performance measurements to reference conditions or translate such results to typical conditions or both is known as the reference cell method. In this reference cell method, the short-circuit current density is assumed to vary linearly with total solar irradiance, which is really not entirely accurate. Also, the translation of the current to a reference solar irradiance condition assumes that the fill factor of the photovoltaic device is independent of irradiance, which also is not entirely correct. Further, the spectral response of the device being tested, including submodules and modules, must be identical to the spectral response of the reference cell, which is unrealistic. Finally, in the reference cell method the photovoltaic device performance is measured with respect to a reference solar irradiance spectrum, temperature, and irradiance level. However, these parameters vary in actual operating conditions. These shortcomings in the reference cell method are especially pertinent to newer photovoltaic devices developed more recently, which employ a variety of materials and contain multiple band gaps.

Another approach to standardizing tests results is to simply measure the spectral solar irradiance incident on the photovoltaic device simultaneously with the performance testing. Such measurements can be made with a suitable spectroradiometer. Then, knowing the spectral distribution of the solar irradiance and the spectral response of the device being tested, the approach is to translate device performance measurements to standard or typical conditions. This approach, of course, assumes that one knows the spectral solar irradiance for standard or typical conditions.

However, spectroradiometers are expensive devices that are difficult to operate and even more difficult to calibrate. Therefore, many photovoltaic researchers find it difficult to operate spectroradiometers, and, even if they learn to operate them, they often cannot afford one. It is also very difficult to use data obtained from spectral radiometers to calculate photovoltaic device performances.

Therefore, recognizing these issues and problems, especially for advanced photovoltaic devices, there has become an identified and articulated need for an improved and less expensive standardized system for measuring and comparing atmospheric optical and spectral solar-irradiance conditions. Such a system should provide economical and simple measurements and readily available, easy-to-use instrumentation to characterize atmospheric optical properties and spectral solar-irradiance conditions during outdoor performance testing of photovoltaic devices. Prior to this invention, there was no system available to fill this need for the community of people who work in the field of research and development of photovoltaic devices.

SUMMARY OF THE INVENTION

Accordingly, it is an object of this invention to provide an economical and easy-to-use method and apparatus for characterizing atmospheric optical properties and spectral solar-irradiance conditions on both an instantaneous and a real-time basis.

It is a more specific object of the present invention to provide low-cost data for spectral solar irradiance on a surface of a given orientation, such as a photovoltaic device, by taking and utilizing a minimum of representative measurements with easy-to-use, readily available instruments.

Another specific object of this invention is to make available a system that can provide real-time spectral data over the entire spectrum from 0.3 to 4.0 $\mu$m.

Still another specific object of this invention is to identify and utilize specific representative measurements from which the entire spectrum characteristics can be determined.

Yet another object of this invention is to identify specific optical characteristics and a method of measuring, correlating, and utilizing such optical characteristics to compare existing outdoor conditions with standard conditions for performance testing of photovoltaic devices.

A further object of this invention is to provide a method of determining whether an outdoor test of a photovoltaic device is being performed in atmospheric optical and spectral solar-irradiance conditions that are close enough to standard conditions so that performance test results can be converted to standard results.

Additional objects, advantages, and novel features of this invention in part are set forth in the description that follows, and in part will become apparent to those skilled in the art upon examination of the following specification or may be learned by the practice of the invention. The objects and advantages of the invention may be realized and attained by means of the instrumentalities and in combinations particularly pointed out in the appended claims.

To achieve the foregoing and other objects and in accordance with the purposes of the present invention as embodied and broadly described herein, the method of this invention may comprise the steps of measuring and determining aerosol optical depth at a selected wavelength, measuring and determining diffuse horizontal skylight to global horizontal photon flux ratio in a selected wave band, and comparing a plot of the product of the aerosol optical depth times relative air mass versus the diffuse horizontal skylight to global horizontal photon flux ratio for actual measured atmospheric optical conditions to the plot of the product of aerosol optical depth times relative air mass versus diffuse horizontal skylight to global horizontal photon flux density ratio of standard atmospheric optical conditions. An indication of how far the plot of actual conditions varies from standard conditions can be provided. The method of this invention also includes the steps of measuring and determining aerosol scattering and absorption properties for three selected wavelengths, diffuse horizontal skylight to global horizontal photon flux density ratio, and precipitable water vapor, and utilizing this data to generate a computer spectral model of actual irradiance, and determining a spectral mismatch factor for correcting actual photovoltaic device responses to standard atmospheric optical condition responses.

The apparatus of this invention generally includes measuring devices connected to microprocessors for carrying out the method of this invention on a real-time basis. Direct normal irradiance measurements are taken at the test site with a multi-wavelength sunphotometer. Direct normal and global horizontal photon flux density measurements are taken at the test site with quantum sensors. Direct normal and global horizontal irradiances over a selected broad band are also taken with silicon-detector-based pyranometers. An indicator is provided to show the variance of measured actual atmospheric optical conditions from standard atmospheric optical conditions.

BRIEF DESCRIPTION OF THE DRAWINGS

The accompanying drawings, which are incorporated in and form a part of the specifications, illustrate the preferred embodiments of the present invention, and together with the description, serve to explain the principles of the invention. In the drawings.

DETAILED DESCRIPTION OF THE PREFERRED EMBODIMENTS

In developing the atmospheric optical calibration system of this invention for providing low-cost measurements of atmospheric optical and spectral solar-irradiance conditions pertinent to photovoltaic device performance measurements, three atmospheric optical properties have been identified as having the most significant bearing on the performance results. These three optical properties include: (1) molecular scattering; (2) aerosol scattering and absorption; and (3) water-vapor absorption.

Figure 1:
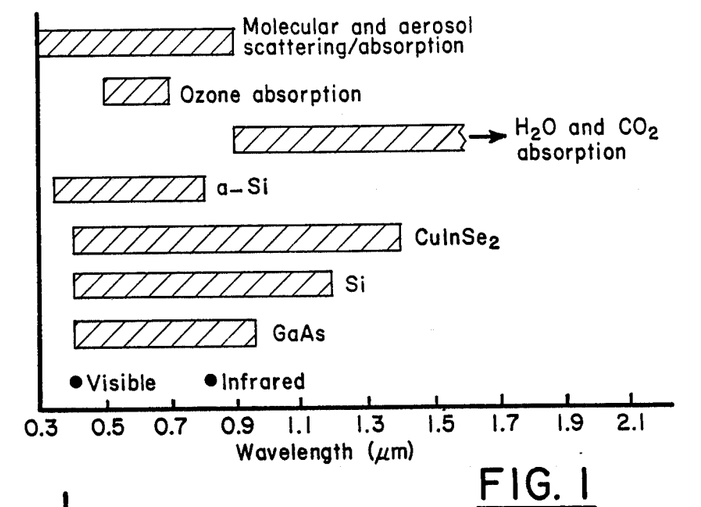
FIG. 1 is a chart showing the wavelength coverage of atmospheric optical properties with some representative photovoltaic devices and materials.

The chart in FIG. 1 summarizes the wavelength coverage of cloudless-sky atmospheric optical properties along with the wavelength absorption ranges of some of the more common representative photovoltaic devices or materials. As shown in FIG. 1, for example, the combination of molecular and aerosol scattering and absorption, along with ozone absorption and water vapor absorption, effectively masks and interferes with the radiant energy in the effective absorption ranges of the common photovoltaic devices.

Appropriate measurements are made according to this invention, which can be used to determine these three atmospheric optical properties of molecular scattering, aerosol scattering and absorption, and water-vapor absorption. These three properties can then be used as inputs to a computer model to generate an accurate estimate of the actual spectral solar irradiance on the photovoltaic device. The atmospheric optical calibration system according to this invention can then be used to compare and better understand the various photovoltaic device outdoor performance measurements by documenting the pertinent atmospheric optical and spectral solar-irradiance conditions on a real-time basis concurrent with the outdoor testing of the photovoltaic devices.

The first of these three optical properties, molecular scattering, is characterized by the extent to which the gaseous molecules of the atmospheric air interfere with and scatter radiation from the sun before it hits the photovoltaic device. Since the molecular density of air is related and proportional to the atmospheric pressure, it can be shown that the spectral optical depth and transmittance of the atmosphere as a result of molecular scattering can be easily and accurately calculated from a measurement of the ambient atmospheric surface pressure. There is an optical depth value due to the air molecules for each wavelength that can be obtained from published tables or a simple equation. The most widely recognized and commonly used optical depth value due to air molecules is known as Rayleigh Optical Depth, $\tau_R$, at sea level ($P_o$, pressure). This Rayleigh Optical Depth, $\tau_R$, can be corrected to other altitudes, $\tau_m$, for a specific location by a proportional multiplier determined by the ratio of ambient air pressure P to standard air pressure at sea level $P_o$ as follows:

$$\tau_m = \frac{P}{P_o} \times \tau_R \qquad (1)$$

Of course, atmospheric pressure P at the specific desired location is essentially a barometer reading. A useable ambient atmospheric pressure P for a specific location can also be obtained from published tables based on elevation above sea level.

The optical depth for ozone scattering, $\tau_o$, in the ozone layer above the earth is also a relatively known value for each wavelength and can be obtained from published tables.

The second property, aerosol scattering and absorption, for purposes of this invention can be determined by two characteristics, (1) Aerosol optical depth at 0.368, 0.500, and 0.862 μm; and
(2) Ratio of diffuse horizontal skylight to global horizontal photon flux density in the range of 0.400 to 0.700 μm.

The first of these characteristics, aerosol optical depth, $\tau_a$, can be determined by subtracting molecular air scattering optical depth, $\tau_m$, and ozone scattering optical depth, $\tau_o$, from the total optical depth of the atmosphere $\tau$. Thus, $$\tau_a = \tau - \tau_m - \tau_o \qquad (2)$$

The molecular air optical depth, $\tau_m$, for a particular location can be obtained from a barometer reading of atmospheric pressure and formula (1) as described above. The optical depth for ozone scattering, $\tau_o$, in the ozone layer above the earth is a known value for each wavelength and can be obtained from published tables. Therefore, the only parameter in equation (2) remaining to be determined is the total optical depth, $\tau$. This total optical depth, $\tau$, can be determined from a ratio of an actual irradiance measurement taken at the testing location to a reference irradiance that would exist if such a measurement were taken outside the atmosphere, which ratio is then corrected for relative air mass for the particular location and for the eccentricity in the earth to sun distance, which varies with the season or time of year.

Figure 2:
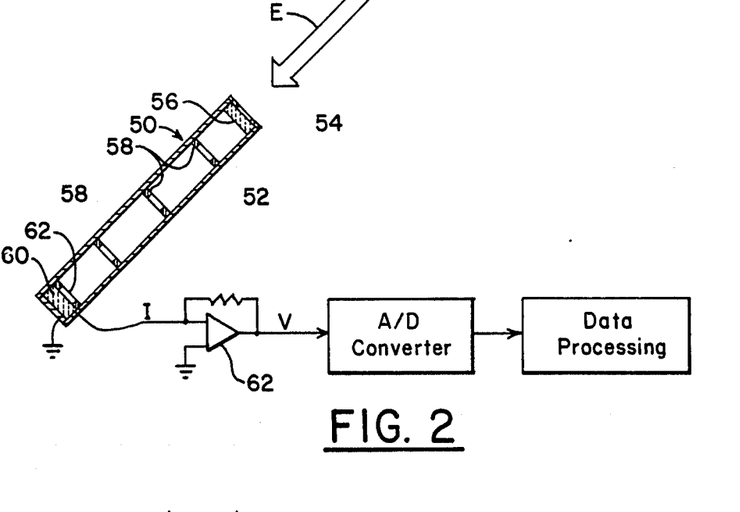
FIG. 2 is an illustration of the principal components of a sunphotometer connected to data processing equipment.

Narrow-band solar-irradiance measurements can be made quite easily with a relatively inexpensive instrument commonly known as a sunphotometer. As illustrated in FIG. 2, a sunphotometer 50 comprises essentially an elongated tube 52 having an aperture 54 on one end for admitting radiant energy E from the sun (not shown). A narrow-band filter 56 can be positioned adjacent the aperture 54 to exclude all but a selected wavelength band of energy as desired to be measured for a particular purpose. A series of baffles 58 can be provided to eliminate internally scattered radiation. A silicon optical detector 60 is positioned at the opposite end of tube 52 behind an internal aperture 62 for converting solar energy to electrical energy. The electrical energy in the form of current I is output by the silicon optical detector 60 in proportion to the irradiance thereof by the solar energy E incident thereon.

The current I produced by the silicon optical detector 60 can then be input to a current-to-voltage converting operational amplifier (op amp) 64, which outputs a voltage V that varies directly as a function of the input current I. Therefore, this output voltage V can be used as data indicative of the the irradiance in the wavelength band admitted by filter 56. Thus, the voltage V can be amplified and, if necessary, converted to digital data by an analog to digital converter and utilized by digital data-processing equipment for computing, using, storing, and displaying such information as optical depth characteristics of the atmosphere.

As discussed above, total optical depth, $\tau$, for a selected wavelength can be determined as a ratio of the actual sunphotometer measurement at the geographic location to an ideal sunphotometer measurement above the earth's atmosphere and corrected for relative air mass and elliptical eccentricity. This relation can be expressed as follows:

$$\tau = \frac{-1}{m_r} \times \ln\left(\frac{\epsilon V}{V_o}\right) \qquad (3)$$

where $m_r$ is the relative air mass, $\epsilon$ is the eccentricity correction, V is the actual sunphotometer measurement at the location, and $V_o$ is the ideal reference sunphotometer measurement outside the atmosphere.

As already discussed above, the actual photometer measurement V for a desired wavelength can be obtained easily and inexpensively with a sunphotometer instrument. The reference $V_o$ can be obtained by converting direct normal extraterrestrial irradation values for the wavelength energy desired from standard reference tables and mathematically converting them to equivalent voltages $V_o$.

The relative air mass $m_r$ is a value indicative of the mass of atmosphere through which solar radiation must travel to reach the geographical location where the test is being conducted, i.e., the slant path through the atmosphere. It is defined as the ratio of the solar irradiance path length through the atmosphere at a given solar zenith angle to the path length through the atmosphere if the sun were in a vertical position directly above the test location with a solar zenith angle of zero. Thus, relative air mass is expressed approximately as the secant of the solar zenith angle $\theta_z$, or $$m_r = \frac{1}{\cos \theta_z}. \qquad (4)$$

The elliptical eccentricity factor $\epsilon$ can be determined as the square of a ratio of a mean distance $r_o$ to the actual distance of the earth to the sun r when the test is performed, or $$\epsilon = \left(\frac{r_o}{r}\right)^2. \quad (5)$$

Therefore, the aerosol optical depth $\tau_a$ can now be determined for a desired wavelength by the equation $$\tau_a = \frac{-1}{m_r} \times \ln\left(\frac{\epsilon V}{V_o}\right) - \frac{P}{P_o}(\tau_R) - \tau_o. \quad (6)$$

The second of the characteristics that is utilized in determining the aerosol scattering and absorption property, as discussed above, is the ratio of diffuse horizontal skylight to global horizontal photon flux density in the selected range of 0.400 to 0.700 μm. The diffuse horizontal skylight is defined as only the radiant energy in terms of number of photons per unit time per unit surface that reach the horizontal surface by a diffuse path, i.e., not including direct sunlight. The global horizontal photon flux density is defined as the radiant energy in terms of number of photons per unit time per unit surface that would reach a surface positioned horizontally at the test location, i.e., including both diffuse and direct sunlight.

The direct sunlight $F_D$ in the desired range of 0.400 to 0.700 μm can be measured easily and inexpensively by a collimated quantum sensor instrument pointed directly at the sun. Such quantum sensors for this 0.400 to 0.700 μm wave band are inexpensive and readily available. For example, the model LI-190SA quantum sensor manufactured by LI-COR, Inc., of Lincoln, Nebr., use colored glass filters to tailor a silicon photodiode to the desired quantum response, and an interference filter is used to provide a sharp cutoff at 0.700 μm. The total radiant energy or global horizontal photo flux density in the desired range of 0.400 to 0.700 μm can be measured easily and inexpensively with a second conventional quantum sensor positioned and leveled horizontally at the test site. The diffuse horizontal skylight $F_s$ can then be determined by subtracting direct horizontal sunlight ($F_D \cos \theta_z$) from global horizontal photon flux density $F_T$, as follows:

$$F_s = F_T - (F_D \cos \theta_z) \quad (7)$$

Therefore, the ratio of diffuse horizontal skylight to global horizontal photon flux density can be expressed as $$\frac{F_s}{F_T} = \frac{F_T - (F_D \cos \theta_z)}{F_T}. \quad (8)$$

Finally, the third property, water-vapor absorption, can be determined by a ratio of the direct beam irradiance at maximum water vapor absorption wavelength to direct beam irradiance at a base wavelength that is not absorbed by water vapor. There are a number of water vapor absorption bands in which radiation is absorbed by water vapor. One of such bands that is large enough to be well defined and relatively easy to measure is between about 0.862 μm and 1.000 μm, with maximum absorption occurring at about 0.942 μm. For purposes of this invention, this maximum water vapor absorption wavelength of 0.942 μm is an effective water absorption band indicator, and 0.862 μm is an effective "window" that is not affected by water vapor.

It has been found, therefore, that precipitable water vapor can be determined for the purposes of this invention as a function of the ratio of direct solar irradiance at 0.862 μm to direct solar irradiance at 0.940 μm. The values of direct solar irradiance at 0.862 μm and at 0.940 μm can, of course, be measured by sunphotometers equipped with narrow-band filters for those wavelengths, respectively, and preferably within band width tolerance of about 0.010 μm. However, this function, to be meaningful and realistic, has to be corrected for a number of factors, including the performance of the particular sunphotometer instruments used, the relative air mass $m_r$, and the ambient pressure P. It also requires correction by at least three additional empirically determined constants to acquire realistic values of precipitable water vapor PWV. The equation for determining precipitable water vapor, PWV, with sunphotometer measurements at the test site of actual irradiance at 0.862 μm, $V_{862}$, and at 0.940 μm, $V_{940}$, respectively, is expressed as follows:

$$PWV = \left(\frac{1}{K_5}\right)\left(\frac{1}{m_r}\right)\left(\frac{P}{P_o}\right)^{k_i}\left[\ln K_3\left(\frac{V_{862}}{V_{940}}\right)\right]^{N_3} \quad (9)$$

where $m_r$ is relative air mass as defined above, P is ambient pressure, $P_o$ is standard pressure at sea level, $K_3$ is an empirically determined constant for the sunphotometer instruments used, and $k_i$, $R_5$, and $N_3$ are constants determined empirically from field measurements.

To provide low-cost data for the instantaneous and real-time spectral solar irradiance on a photovoltaic device under test according to this invention, one can use atmospheric optical scattering, absorption, and water vapor data above as inputs to a spectral solar irradiance computer model. Specifically, it can be shown that by acquiring such optical scattering, absorption, and water vapor data at these strategically selected wavelength bands in the solar spectrum and using this data as inputs to a mathematical spectral solar irradiance model, one can generate an estimate of actual solar irradiance over the entire spectrum incident on the photovoltaic device under test. Further, these data can be used to make very low-cost, real-time comparisons of actual outdoor optical and spectral solar-irradiance conditions existing at the testing time and location with standard conditions. In other words, this latter feature of this invention can provide both instantaneous and real-time information about actual atmospheric optical and spectral solar-irradiance conditions as compared to standard conditions when and where a person wants to test a photovoltaic device outdoors.

Therefore, a person can determine, when he sets up his outdoor test, whether he has standard atmospheric optical and spectral solar-irradiance conditions or whether his actual conditions are within a range close enough to standard conditions so that his actual performance data can be corrected to standard. If not, he might as well not waste his time running the test until the actual atmospheric conditions improve. This comparison, according to this invention, can even be set up in a simple "go" or "no go" indicator format, such as a green light display to go ahead with the test when conditions are close to standard and a red light display when they are not close enough.

Figure 3:
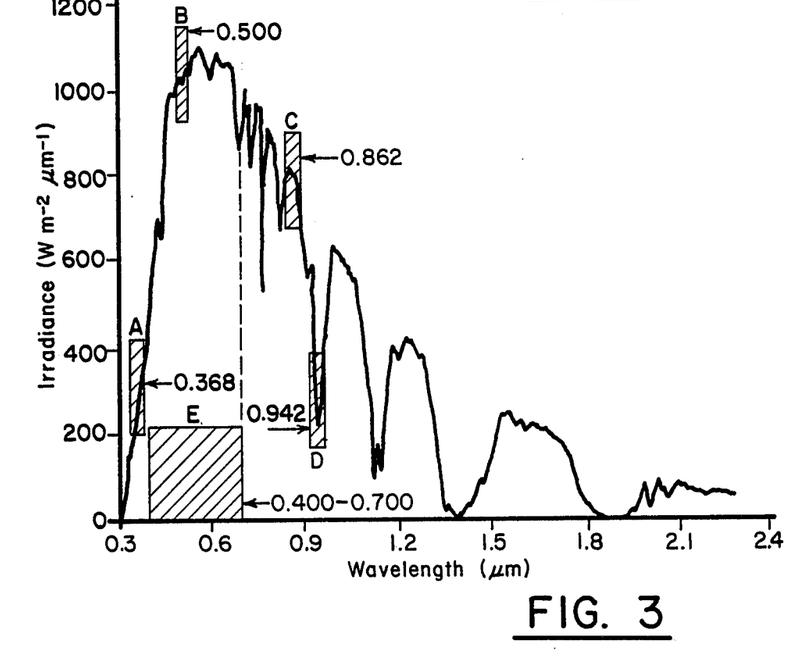
FIG. 3 is an illustration of a solar spectrum with certain input channel information for this invention superimposed thereon.

The strategically selected wavelength bands for data acquisition according to this invention are shown in FIG. 3 superimposed on a representative actual irradiance curve over the solar spectrum illustrated here from 0.3 to 2.4 μm. These selected bands are designated as "channels" A, B, C, D, and E because measurements in these bands are input directly into the data processor equipment as channels of input data. As discussed above, measurements can be made easily and inexpensively in these bands or channels by sunphotometers 50, the variable current outputs of which are converted to variable voltage outputs V by op amps 64, as illustrated in FIG. 2.

The bands or channels A, B, and C are selected as strategic measurements V proportional to the actual direct normal irradiance for use in determining total optical depth $\tau$ in equation (3) and then aerosol optical depth $\tau_a$ in equation (6). The bands for channels A and B were selected as 0.368 μm and 0.500 μm, respectively, because they consistently represent the typical nearly linear ascending slope of the initial part of the representative irradiance curve, as shown in FIG. 3, with the 0.500 μm measurement being near maximum irradiance level where the curve begins its generally descending slope. The band for channel C was selected at 0.862 μm because it not only represents a typical point on the generally descending slope part of the irradiance curve, but it is also the point of no water vapor absorption or "window" as discussed above for the determination of precipitable water vapor PWV factor. Therefore, the channel C measurement is used conveniently in determining both aerosol scattering and water-vapor absorption.

Consequently, the optical filter 56 in the sunphotometer 150 for channel A passes a narrow band of radiation about 0.368±0.005 μm, and the output voltage $V_{368}$ is a measurement of direct normal irradiance in that band for channel A. Likewise, the optical filter 56 in the sunphotometer 250 for channel B passes a narrow band of radiation about 0.500±0.005 μm, and the output voltage $V_{500}$ is a measurement of direct normal irradiance in that band for channel B. Similarly, the sunphotometer 350 for channel C is fitted with a narrow-band filter 56 that passes about 0.862±0.005 μm radiation, and the output voltage $V_{862}$ is a measurement of direct normal irradiance in that band for channel C.

The band for channel D measurement is selected at 0.942 μm because, as discussed above, it is the point of maximum radiation absorption by water vapor in the well-defined water vapor absorption band bounded on one edge by the 0.862 μm "window" through the water vapor. Therefore, the sunphotometer 450 for this channel D is fitted with a narrow-band filter 56 that passes about 0.942±0.005 μm radiation, and the output $V_{942}$ is a measurement of direct normal irradiation for this channel D.

From these four data points taken at the above-described bands for channels A, B, C, and D, the rest of the spectral irradiance curve can be predicted as described above. According to this approach, low-cost, real-time spectral data can be provided over the entire spectrum from 0.30 to 4.00 μm. Therefore, the need for a spectroradiometer can be eliminated. Further, as discussed above, the channel A, B, and C measurements can be used to determine turbidities or aerosol scattering and absorption properties, while the channel C and D measurements can be used to determine precipitable or atmospheric water vapor. These channels can also be used, along with photon flux density ratios, to correct actual photovoltaic device response to standard optical atmospheric response, i.e., to the response that would be expected of the photovoltaic device under standard optical atmospheric and spectral solar-irradiance conditions.

As discussed above, optical depths determined by channels A, B, and C measurements provide just one type of component of the aerosol scattering and absorption property. The other component is the ratio of diffuse horizontal skylight to global horizontal photon flux density. As mentioned above, this component can be obtained from quantum sensors 70 and 550 measurements. The collimated quantum sensor 550 for this purpose measures photon flux density in the band of 0.400 to 0.700 μm and is directed toward the sun. Therefore, its output $F_D$ is a measurement of direct normal photon flux density in the 0.400 to 0.700 μm band. This output $F_D$ is designated as channel E. The quantum sensor 70 also has a 0.400 to 0.700 μm band filters, but it is positioned horizontally. Its output $F_T$, designated as channel G, is a measure of total radiant energy or global horizontal photon flux density in the 0.400 to 0.700 μm band. These channel E and G measurements define the real-time photon flux density environment in which the photovoltaic device is tested. The diffuse horizontal skylight and the ratio of diffuse horizontal skylight to global horizontal photon flux density can therefore be obtained from these channel E and G measurements according to equations (7) and (8) described above.

The band range of 0.400 to 0.700 μm for these photon flux measurements of channels E and G was chosen for several reasons, including: (1) The availability of inexpensive sensors in this range because, since this range is the photosynthesis range of plants, quantum sensors for this range are already used by plant biologists to measure available photosynthesis energy; (2) This band range also covers a significant portion of the solar spectrum, especially photon flux, utilized by many photovoltaic devices, including amorphous silicon; and (3) Photon flux measurement in this range is insensitive to changes in atmospheric water vapor content, as opposed to the insolation measurement, and is characteristic of many photovoltaic devices. This measurement is intended to complement the conventional measurement of broad-band solar irradiance, or insolation, incident on the photovoltaic device. Also, it is significant that this ratio of diffuse horizontal skylight to global horizontal photon flux density according to this invention is very sensitive to the overall aerosol scattering and absorption properties of the atmosphere.

Figure 4:
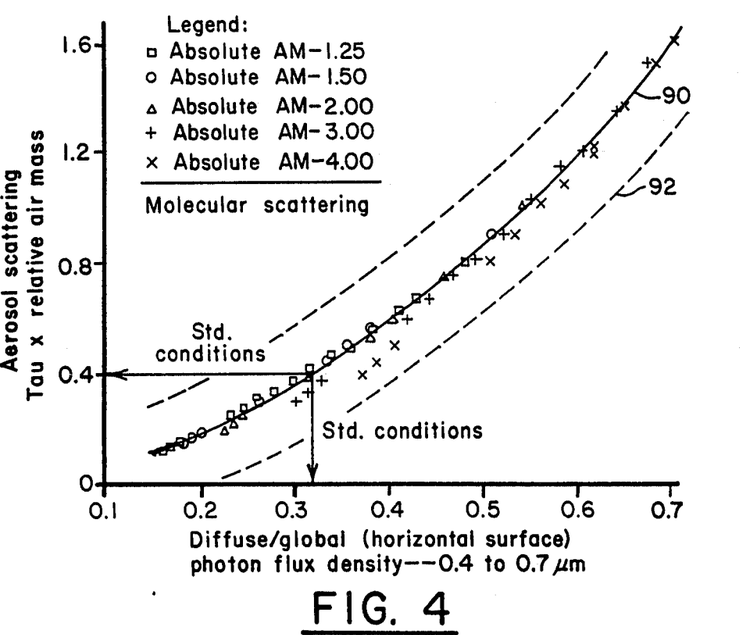
FIG. 4 is a graph illustrating the functional relationship (modeled) between aerosol optical depth and ratio of diffuse horizontal skylight to global horizontal photon flux density for standard optical atmospheric conditions for a range of absolute air masses for comparison to actual conditions according to this invention.

A significant feature of this invention is the use of aerosol optical depth, $\tau_a$, and the ratio of diffuse to global horizontal photon flux density as determined above to compare actual existing outdoor optical atmospheric conditions to standard optical atmospheric conditions on a low-cost, instantaneous, and real-time basis. This feature is illustrated in FIG. 4, which shows the product of the 0.500 μm aerosol optical depth $\tau_a$ and the relative air mass (slant path through the atmosphere) plotted versus the ratio of diffuse to global horizontal photon flux density (0.400 to 0.700 μm) for a range of absolute air masses, i.e., molecular scattering conditions. This functional relationship shows that for cloudless-sky conditions and absolute air masses less than 3 or 4, the very simple measurement of the diffuse/flobal horizontal photon flux density ratio according to this invention is a very sensitive indicator of aerosol scattering and absorption conditions.

For example, FIG. 4 shows the standard atmospheric optical scattering conditions used to generate standard (reference) solar-irradiance spectra as used by the photovoltaic industry. By using the functional relationship shown in FIG. 4, the simple diffuse/global horizontal photon flux density ratio measurement and the sunphotometer measurement of aerosol optical depth $\tau_a$ at 0.500 μm, one can make the low-cost, real-time comparisons between existing actual outdoor optical conditions, including cloudy skies, and standard conditions. Specifically, if the plot of actual aerosol optical depth $\tau_a$ at 0.500 μm times the relative air mass $m_r$ versus actual diffuse/global horizontal surface photon flux density ratio falls above the standard condition line 90, then there is not enough aerosol scattering in the air; i.e., it is clearer than standard atmospheric conditions. On the other hand, if the plot of these values falls below the standard condition line 90, then there is too much diffuse horizontal skylight for standard conditions, e.g., too cloudy or, perhaps, too polluted.

There is a practical range 92 on either side of the standard condition line 90 in which photovoltaic test results can be corrected according to this invention to indicate results that would be expected at standard conditions. Therefore, if actual atmospheric optical conditions measured according to this invention fall within the range 92, outdoor testing of the photovoltaic device can proceed. However, if the actual conditions fall outside range 92, then outdoor testing of the photovoltaic device would be futile because the test results could not be compared to standard conditions in a meaningful manner. Therefore, as mentioned above, the atmospheric optical calibration system according to this invention can include data for a preset satisfactory range 92, e.g., a zero to fifty percent variance from the standard line 90, and a data processor can be programmed to compare actual values from measurements with these preset range data. The microprocessor or computer can also be programmed to actuate a "go" indicator, such as a green light, when the comparison shows actual conditions in the acceptable range 92, and to actuate a "no go" indicator, such as a red light, when the comparison shows actual conditions outside the acceptable range 92. Of course, other conveniences, such as an amber light indicator for borderline conditions or a range gauge to indicate actual position in relation to standard, can also be incorporated within the scope of this invention.

If the actual optical atmospheric conditions are "go" according to this invention, the outdoor test of the photovoltaic device can proceed. Concurrently, the spectral input data described above are measured, and fed into microprocessors to derive the aerosol scattering and absorption, direct skylight to global horizontal photon flux ratio, and precipitable water vapor properties on a real-time basis. These properties are in turn used as input for a mathematical spectral model to derive a computer-generated model of the solar spectrum at the test site on a real-time basis. This solar spectrum model can be converted to a tilt model that represents the spectral irradiation on a tilted plane, such as the plane in which the photovoltaic device under test is tilted. The Solar Energy Research Institute (SERI) SPECTRAL-2 computer model described in R. E. Bird and C. J. Riordan, *Simple Solar Spectral Model for Direct and Duffuse Irradiance on Horizontal and Tilted Planes at the Earth's Surface for Cloudless Atmospheres*, 25 J. OF CLIMATE AND APPL. METEOROLOGY, No. 1, at 87-97 (January 1986), is an example of a computer model that can be used for generating the spectral irradiance data for horizontal and tilted planes for use in this invention. Horizontal spectral irradiance to tilted plane irradiance conversion is also described in R. Perez and R. Stewart, *Solar Irradiance Conversion Models*, PROC. PHOTOVOLTAICS AND INSOLATION MEASUREMENTS WORKSHOP, SERI/CP-215-2713 (June 30–July 3, 1985).

The converted tilt plane solar irradiance model can then be used along with the actual photovoltaic device test responses and the device dimensions to translate the actual device performance measurements to reference condition response values. Such correction can be made by using a correction factor, such as the mismatch parameter described in C. R. Osterwald, *Translation of Device Performance Measurements to Reference Conditions*, PROC PHOTOVOLTAICS AND INSOLATION MEASUREMENTS WORKSHOP, SERI/CP-215-2713 (June30–July 3, 1985).

Figure 5:
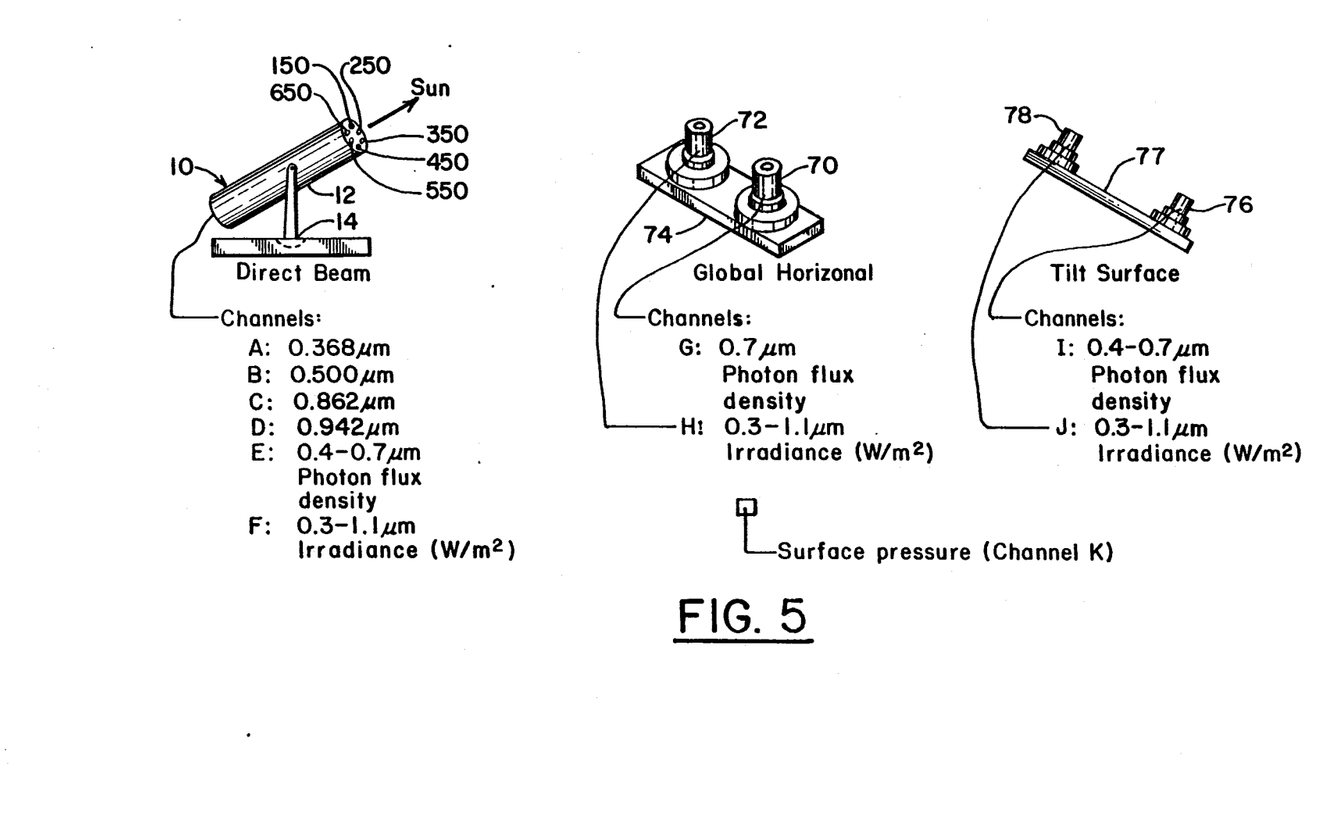
FIG. 5 illustrates the components and channels of data for the atmospheric optical calibration system according to this invention.

FIG. 5 illustrates the instrumentation for making the measurements for the atmospheric optical calibration system of this invention. The direct normal irradiance and direct photon flux density measurements, as well as global irradiance, if desired, are made with a sunphotometer assembly 10 directed at the sun. It has the sunphotometers 150, 250, 350, and 450, as well as quantum sensor 550 and a silicon-detector-based pyranometer 650, all clustered in an elongated housing 12 and pointed in the same direction. The housing 12 is mounted on a pivotal base 14, which is equipped with automatic sun-tracking capability for keeping the sunphotometers and quantum sensors in housing 12 pointed directly at the sun.

The sunphotometers 150, 250, 350, and 450 produce the above-described narrow-band measurements for channels A, B, C, and D data, respectively. The direct normal photon flux density measurements in the band of 0.4–0.7 μm for channel E are produced by the quantum sensor 550. The channel F measurement of broad band direct normal irradiance in terms of total energy per unit time per unit area or power per unit area in the range of 0.3 to 1.1 μm is provided by the silicon-detector-based pyranometer 650, such as a model LI-200SA Pyranometer Sensor manufactured by LI-COR, Inc., of Lincoln, Nebr.

The global horizontal photon flux density measurements for channels G and H are provided by a quantum sensor 70 and a silicon-detector-based pyranometer 72, both of which are mounted on a horizontal base 74. The quantum sensor 70 provides global horizontal photon flux density in the 0.4 to 0.7 μm band for channel G data. The pyranometer 72 provides horizontal irradiance in the 0.3 to 1.1 μm broad band for channel H data.

It is appropriate to mention here that while the ratio of diffuse horizontal skylight to global horizontal photon flux density for the 0.400 to 0.700 μm band is satisfactory for purposes of input to the computer spectral model as discussed above, results over the broad spectrum can be checked by also utilizing the measured direct normal and global horizontal irradiance in the 0.3 to 1.1 μm band as a check in the spectral model. The channels F and H data inputs are used for this purpose.

Also, as a further check on the conversion model of the spectral model converted to spectral irradiation on the tilted photovoltaic device surface, 0.4 to 0.7 μm photon flux density and the 0.3 to 1.1 μm irradiance of the outdoor test site can be taken on the same tilt plane as the photovoltaic device under test. For example, the tilt plane photon flux density in the 0.4 to 0.7 μm band can be measured by another quantum sensor 76 mounted on the tilted base 77. This tilt quantum sensor 76 measurement is put out as channel I data. Also, the tilt irradiance measurement in the band 0.3 to 1.1 μm is provided on a channel J channel by pyranometer 78 mounted on the tilted base 77.

Figure 6A:
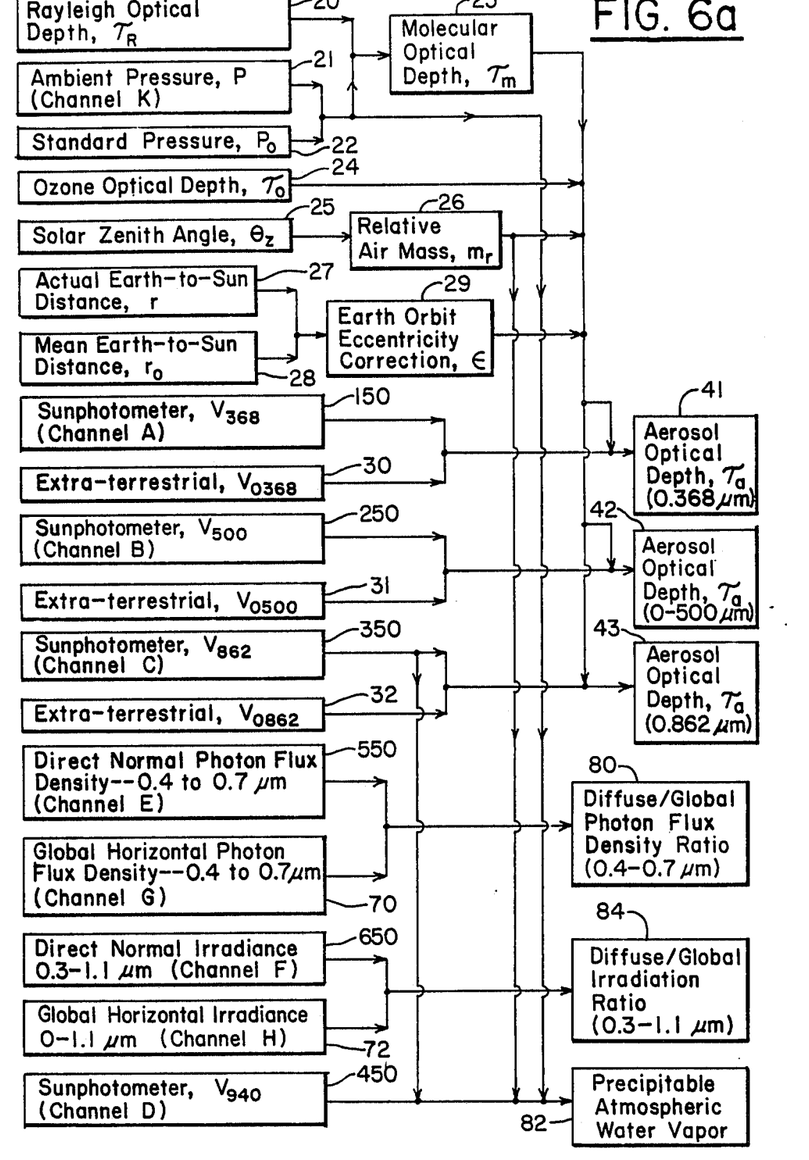
FIGS. 6a and 6b comprise together a flow diagram of the inputs and steps of this invention to produce the desired comparison of actual optical atmospheric conditions with standard conditions and for obtaining photovoltaic responses converted to standard condition values.
Figure 6B:
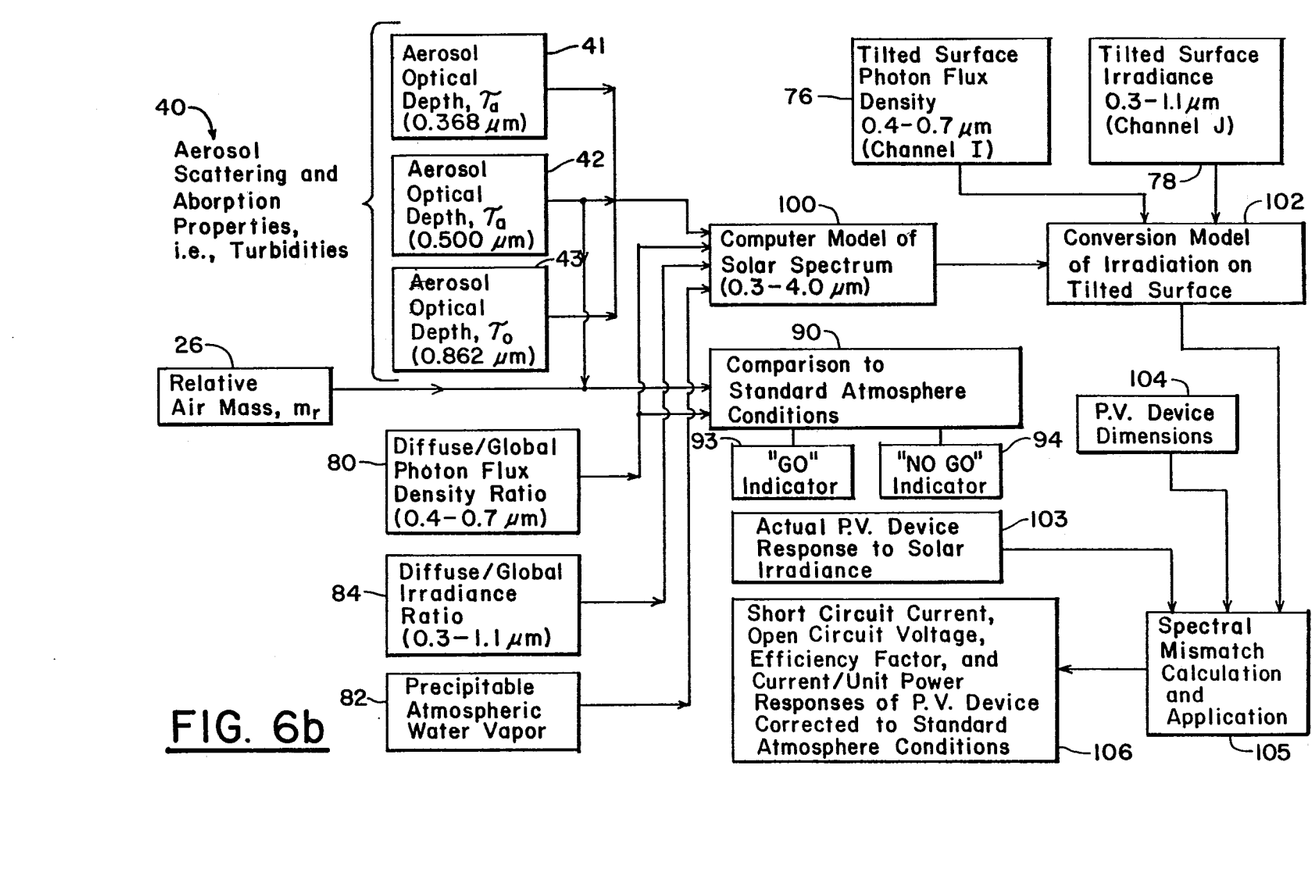

The composite flow chart illustrated in FIGS. 6a and 6b shows how the various parameters described above are used to obtain the desired results of photovoltaic device response corrected to standard atmosphere values. The Rayleigh optical depth 20, ambient pressure 21, and standard atmospheric pressure 22 are used to calculate a molecular optical depth 23, according to equation (1). The ozone optical depth 24 is obtainable from a standard table, as is the solar zenith angle 25 for various locations. The relative air mass 26 is calculated by equation (4). Likewise, the actual earth-to-sun distance 28 is available in standard tables, so the earth orbit eccentricity 29 can be calculated by equation (5).

The theoretical extraterrestrial sunphotometer values 30, 31, and 32 for the wavelengths 0.368 μm, 0.500 μm, and 0.862 μm, respectively, are available from standard tables, and can be converted to voltage values corresponding to the scale of actual sunphotometer voltage outputs for those values as required for use in equation (6). The actual sunphotometer data for channels A, B, C, and D are measured with the sunphotometers 150, 250, 350, 450, and respectively, as described above. The 0.4 to 0.7 μm direct normal photon flux density for channel E is provided by quantum sensor 550, and the global horizontal photon flux density for channel G is provided by quantum sensor 70.

The aerosol scattering and absorption properties 40, also called turbidities, are the combination of aerosol optical depths 41, 42, and 43 of the 0.368 μm, 0.500 μm, and 0.862 μm wavelengths, respectively. These aerosol optical depths are calculated by equation (6) for each wavelength 0.368 μm, 0.500 μm, and 0.862 μm. These turbidities factors 40 are utilized in modeling a solar spectrum irradiance 100, and the 0.500 μm optical depth 42 is used as a data input for comparison to standard conditions 90, as described above.

The ratio 80 of diffuse horizontal skylight to global horizontal photon flux density for 0.4 to 0.7 μm is calculated according to equation (8) with channels E and G data from the direct normal quantum sensor 550 and the global horizontal quantum sensor 70. This diffuse/global photon flux ratio 80 is used as data input to the computer model solar spectrum 100 as well as in the comparison to standard atmosphere conditions 90.

As discussed above, where the relationship between actual 0.500 μm aerosol optical depth 42 and diffuse/global photon flux ratio 80 varies too much from standard conditions 90, a "no go" signal 94 can be actuated to warn that the test results in those actual optical atmospheric conditions are not correctable to standard, and thus may be of little value. On the other hand, if this relationship is close enough to standard conditions 90, a "go" signal 93 can be actuated to indicate test results will be acceptable and correctable to standard conditions.

The precipitable atmospheric water vapor 82 is calculated according to the equation (9) with data input from the channels C and D sunphotometers 350 and 450 for 0.862 μm and 0.940 μm, respectively, along the relative air mass 26. This precipitable water vapor is also used as input data for the computer model solar spectrum 100.

The computer model solar spectrum 100 derived from aerosol scattering and absorption properties or turbidities 40, diffuse/global photon flux ratio 80, and precipitate water vapor 82 data inputs results in data defining a solar spectrum that closely approximates the actual outdoor solar irradiance. Also, as discussed above, a ratio 84 of diffuse horizontal skylight to global horizontal irradiance in the 0.3 to 1.1 μm band can also be input to the computer model 100 to increase accuracy of the computer model over the 0.3 to 4.0 μm spectrum band. This ratio 84 can be obtained similar to the ratio 80, except the inputs are direct normal irradiance 650 over the band of 0.3 to 1.1 μm from channel F and global horizontal irradiance 72 over the band of 0.3 to 1.1 μm from channel H.

This computer model solar spectrum 100 is then converted to a model 102 of irradiation on a surface tilted to the same angular orientation as the photovoltaic device under test. The accuracy of the conversion model 102 can be checked by comparing the conversion model photon flux density and irradiation for at tilted surface with actual measured photon flux density and irradiance on a tilted surface. For example, a quantum sensor 76 and a pyranometer 78 can be mounted on a surface 77 and tilted to the same orientation as the photovoltaic device under test. The actual photon flux density in the 0.4 to 0.7 μm band for channel I measured by the quantum sensor 76 and the actual irradiance in the 0.3 to 1.1 μm band for channel J measured by pyranometer 78 can be compared to corresponding conversion model 102 values. If they vary more than an acceptable tolerance, then adjustments can be made to correct the conversion model 102 for better accuracy.

This conversion model 102 is then used with a spectral mismatch correction factor 105 and the actual photovoltaic device dimensions 104 to modify or "correct" actual photovoltaic device responses 103 to "spectrally corrected" or standard condition responses 106. These spectrally corrected responses 106 are essentially the responses that the particular photovoltaic device under test would produce if the test could be conducted at standard optical atmospheric conditions 90. Such "spectrally corrected" responses can include short-circuit current, open-circuit voltage, efficiency factor, power output, and the like, and they can be displayed during the outdoor test on a real-time basis. Such performance responses for a particular photovoltaic device that are "spectrally corrected" for standard optical atmospheric conditions can then be compared and evaluated on a common basis with "spectrally corrected" performance responses of other photovoltaic devices. Alternatively or concurrently, the spectral-mismatch correction values 105 for converting the actual responses to spectrally corrected responses can be displayed on a real-time basis.

During a photovoltaic device test, data can be acquired at frequent regular intervals, such as every 15 minutes starting at the nearest quarter hour after one hour after sunrise and ending at the nearest quarter hour before one hour before sunset. All of the measured parameters can be entered continuously and automatically to microprocessors programmed to make the calculations and comparisons described above. Actual channel inputs can be timed closely, such as every two seconds for stability. Optional keyboard entries can also be made, and all data can be recorded. All input and output data can be printed or displayed on a real-time basis.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to falling within the scope of the invention as defined by the claims that follow.

The embodiments of the invention in which an exclusive property or privilege is claimed are defined as follows:

1. The method of comparing actual atmospheric optical conditions to standard atmospheric optical conditions on instantaneous and real-time basis, comprising the steps of:
   measuring actual aerosol optical scattering properties and multiplying said properties by relative air mass;
   measuring and determining actual diffuse horizontal skylight and global horizontal photon flux density and determining the ratio of diffuse horizontal skylight to global horizontal photon flux density; and
   comparing a plot of the product of actual aerosol scattering properties times relative air mass versus the actual diffuse horizontal skylight to global horizontal photo flux density ratio with a plot the product of standard condition aerosol scattering properties times relative air mass versus standard condition diffuse horizontal skylight to global horizontal photon flux density ratio.

2. The method of claim 1, including the step of measuring actual aerosol optical scattering properties by measuring and determining actual aerosol optical depth.

3. The method of claim 2, including the step of measuring and determining aerosol optical depth by measuring and determining total optical depth and subtracting molecular optical depth and ozone optical depth from said total optical depth.

4. The method of claim 3, including the step of measuring and determining total aerosol optical depth by measuring direct normal irradiance on earth at a selected wavelength and correcting a ratio of direct normal irradiance to extraterrestrial direct normal irradiance at the same selected wavelength and correcting said ratio for relative air mass and ellipical eccentricity according to the formula $$\tau = \frac{-1}{m_r} \times \ln\left(\frac{\epsilon V}{V_o}\right)$$

where $\tau$ is total aerosol optical depth, $m_r$ is relative air mass, $\epsilon$ is the eccentricity correction, V is the measure of irradiance at the selected wavelength, and $V_o$ is the extraterrestrial irradiance at the selected wavelength.

5. The method of claim 4, including the step of measuring said direct normal irradiance at a selected wavelength of about 0.500 μm.

6. The method of claim 5, including the step of measuring said direct normal irradiance at the selected wavelength of about 0.500 μm with a sunphotometer equipped with a filter that passes only about 0.500 μm light and is pointed directly at the sun.

7. The method of claim 1, including the step of measuring actual diffuse horizontal skylight by measuring direct normal photon flux density in a selected wave band, measuring a global horizontal photon flux density in the same selected wave band, and subtracting the direct normal photon flux density from the global horizontal photon flux density.

8. The method of claim 7, including the steps of measuring the direct normal photon flux density and the global horizontal photon flux density in the selected wave band of about 0.4 to 0.7 μm.

9. The method of claim 7, including the steps of measuring the direct normal photon flux density with a quantum sensor device having a silicon photodiode pointed directly at the sun and measuring the global horizontal photon flux density with a quantum sensor device having a silicon photodiode positioned horizontally on the earth's surface.

10. The method of claim 1, including the steps of:
    measuring direct normal irradiance at a selected wavelength with a sunphotometer and measuring ambient pressure with a barometer device, feeding these irradiance and ambient pressure measurements into a microprocessor along with predetermined values for relative air mass, eliptical eccentricity correction factor, extraterrestrial irradiance at the selected wavelength, standard sea level pressure, Rayleigh optical depth, and ozone optical depth, which microprocessor is programmed to calculate aerosol optical depth according to the formula $$\tau_a = \frac{-1}{m_r} \times \ln\left(\frac{\epsilon V}{V_o}\right) - \frac{P}{P_o}(\tau_R) - \tau_o$$

where $\tau_a$ is aerosol optical depth, $m_r$ is relative air mass, $\epsilon$ is the eliptical eccentricity correction factor, V is the irradiance measurement, $V_o$ is the extraterrestrial irradiance value, P is the ambient pressure measurement, $P_o$ is the sea level pressure, $\tau_R$ is the Rayleigh optical depth, and $\epsilon_o$ is the zone optical depth;

measuring direct normal photon flux density in a selected wave band with a quantum sensor pointed directly at the sun, measuring global horizontal photon flux density in the selected wave band with a quantum sensor oriented horizontal on the surface of the earth, feeding said direct normal and global horizontal measurements into a microprocessor programmed to calculate the ratio of diffuse horizontal skylight to global horizontal photon flux density according to the formula $$\frac{F_s}{F_T} = \frac{F_T - (F_D \cos\theta_z)}{F_T}$$

where $F_D$ is direct normal photon flux density, $F_S$ is diffuse horizontal skylight, and $F_T$ is the global horizontal photon flux density;

feeding the aerosol optical depth, relative air mass, and ratio of diffuse horizontal skylight to global horizontal photon flux density into a microprocessor programmed to compare a plot of the product of this aerosol optical depth times relative air mass versus this ratio of diffuse horizontal skylight to global horizontal photon flux density for the measured conditions with a plot of standard atmospheric optical conditions of the product of aerosol optical depth times relative air mass versus the ratio of diffuse horizontal skylight to global horizontal photon flux density for the standard atmospheric optical conditions; and displaying an indication of the comparison between actual and standard conditions.

11. The method of claim 10, including the step of displaying a "go" indicator when said comparison shows actual atmospheric optical conditions to be within a selected range near standard atmospheric optical conditions, and displaying a "no go" indicator when said comparison shows actual atmospheric optical conditions to be outside said selected range.

12. The method of claim 10, including the steps of measuring said direct normal irradiance at a selected wavelength of about 0.5 μm and measuring said direct normal photon flux density and said global horizontal photon flux density in the range of about 0.4 to 0.7 μm.

13. The method of converting actual outdoor photovoltaic device test performance to standard atmospheric optical condition results on a real-time basis concurrent with the test, comprising the steps of:

measuring ambient pressure, direct normal irradiance at about 0.368 μm, direct normal irradiance at about 0.500 μm, and direct normal irradiance at about 0.862 μm at the test site concurrently with the photovoltaic device test;

feeding said ambient pressure P, direct normal irradiance V at 0.368 μm, 0.500 μm, and 0.862 μm wavelengths measurements as data input to a microprocessor on a continuous basis, which microprocessor has stored therein data for Rayleigh optical depth $\tau_R$, standard sea level pressure $P_o$, ozone optical depth $\tau_o$, relative air mass $m_r$, earth orbit eccentricity correction factor $\epsilon$, and extraterrestrial direct normal irradiance $V_o$ for 0.368 μm, 0.500 μm, and 0.862 μm wavelengths and is programmed to calculate aerosol optical depth $\tau_a$ for each 0.368 μm, 0.500 μm, and 0.862 μm wavelength according to the formula $$\tau_a = \frac{-1}{m_r} \times \ln\left(\frac{\epsilon V}{V_o}\right) - \frac{P}{P_o}(\tau_R) - \tau_o;$$

measuring direct normal photon flux density for the wave band of about 0.4 to 0.7 μm, global horizontal photon flux density for the wave band in the range of about 0.4 to 0.7 μm, direct normal irradiance for the wave band in the range of about 0.3 to 1.1 μm, and global horizontal irradiance in the wave band of about 0.3 to 1.1 μm at the test site concurrently with the photovoltaic device test;

continuously feeding said measurements of direct normal and global horizontal photon flux density over about 0.4 to 0.7 μm and of said direct normal and global horizontal irradiance over about 0.3 to 1.1 μm on a continuous basis into a microprocessor that is programmed to calculate the ratio of diffuse horizontal skylight to global horizontal photon flux density by subtracting photon flux density by subtracting direct normal photon flux density over 0.4 to 0.7 μm and dividing the difference by the global horizontal photon flux density over 0.4 to 0.7 μm and to calculate the ratio of diffuse irradiance to global horizontal photon flux density over 0.4 to 0.7 μm and to calculate the ratio for diffuse irradiance to global horizontal irradiance by subtracting the direct normal irradiance over 0.3 to 1.1 μm from the global horizontal irradiance over 0.3 to 1.1 μm and dividing the difference by the global horizontal irradiance over 0.3 to 1.1 μm;

measuring the direct normal irradiance at about 0.940 μm wavelength at the test site concurrently with the photovoltaic device test;

continuously feeding said measured direct normal irradiance $V_{940}$ at about 0.940 μm wavelength along with said measured direct normal irradiance $V_{862}$ at about 0.862 μm in to a microprocessor that has stored therein the relative air mass $m_r$, ambient pressure P, standard sea level pressure $P_o$, and constants $k_i$, $K_3$, $K_5$ and $N_3$, which microprocessor is programmed to calculate precipitable water vapor PWV according to the formula $$PWV = \left(\frac{1}{K_5}\right)\left(\frac{1}{m_r}\right)\left(\frac{P}{P_o}\right)^{kl}\left[\ln K_3\left(\frac{V_{862}}{V_{940}}\right)\right]^{N_3};$$

continuously feeding said aerosol optical depths for the wavelengths of about 0.378, 0.500, and 0.862 μm, said diffuse horizontal skylight to global horizontal photon flux ratio for about 0.4 to 0.7 μm wave band, said diffuse irradiance to global horizontal irradiance ratio for about 0.3 to 1.1 μm wave band, and said precipitable water vapor as input data into a microprocessor programmed to generate a computer spectral model of solar irradiance from said input data at the test site over the spectrum from about 0.3 to 4.0 μm;

converting said computer spectral model to a model of irradiation on a tilted surface at the test site having an angular orientation the same as the angular orientation of the photovoltaic device being tested;

continuously calculating the spectral mismatch of the photovoltaic device being tested.

14. The method of claim 13, including the steps of:

measuring the direct normal irradiance for the wavelength of about 0.368 μm with a sunphotometer equipped with a filter that passes only about 0.368 μm light and pointed directly at the sun;

measuring the direct normal irradiance for the wavelength of about 0.500 μm with a sunphotometer equipped with a filter that passes only about 0.500 μm light and pointed directly at the sun;

measuring the direct normal irradiance for the wavelength of about 0.862 μm with a sunphotometer equipped with a filter that passes only about 0.862 μm light and pointed directly at the sun;

measuring the direct normal irradiance for the wavelength of about 0.940 μm with a sunphotometer equipped with a filter that passes only about 0.940 μm light and pointed directly at the sun;

measuring the direct normal photon flux density with a collimated quantum sensor equipped with a silicon photodiode and filters that pass only light in the range of about 0.4 to 0.7 μm and pointed directly at the sun;

measuring the global horizontal photon flux density with a quantum sensor equipped with a silicon photodiode and filters that pass only light in the range of about 0.4 to 0.7 μm and oriented horizontal to the earth surface;

measuring the direct normal irradiance in the wave band of about 0.3 to 1.1 μm with a collimated silicon-detector-based pyranometer pointed directly at the sun; and measuring the global horizontal irradiance in the wave band of about 0.3 to 1.1 μm with a silicon-detector-based pyranometer oriented horizontal to the earth surface.

15. The method of claim 14, including the steps of measuring the photon flux density in the wave band of about 0.4 to 0.7 μm and the irradiance in the wave band of about 0.3 to 1.1 μm on a surface tilted an angular orientation matching the angular orientation of the photovoltaic device being tested and checking the conversion model photon flux density and irradiance against these measure values of photon flux density and irradiance on the tilted surface.

16. A method of determining the character and quantity of skylight solar irradiance available at a particular location on a real-time basis where outdoor testing of a solar device is being conducted, comprising the steps of:

measuring environmental outdoor optical skylight conditions including molecular scattering, aerosol scattering and absorption, the ratio of diffuse horizontal skylight to global horizontal photon flux density, and water vapor absorption;

generating a signal from said measured optical conditions indicative of the spectral solar irradiance available at the location of the solar device; and generating a spectral-mismatch correction factor for correcting actual performance results of the solar device in response to actual outdoor irradiation at the test location to standard atmospheric optical condition performance results for the solar device being tested.

17. Apparatus for comparing actual atmospheric optical conditions at an outdoor location for testing a photovoltaic device with standard atmospheric optical conditions, comprising:

means for measuring and determining aerosol optical depth at said testing locations;

means for measuring and determining the ratio of diffuse horizontal skylight to global horizontal photon flux density at the testing location; and means for comparing a plot of the product of the actual aerosol optical depth times relative air mass versus the diffuse horizontal skylight to global horizontal photon flux ratio at the testing location with a plot of the product of aerosol optical depth times relative air mass versus the diffuse horizontal skylight to global horizontal photon flux ratio for standard atmospheric optical conditions.

18. The apparatus of claim 17, including signal means for indicating how far the plot for actual atmospheric optical conditions varies from the plot for standard atmospheric optical conditions.

19. The apparatus of claim 17, wherein said means for measuring and determining aerosol optical depth includes a sunphotometer for measuring direct normal irradiance at about 0.5 μm, and wherein said means for measuring and determining the ratio of diffuse horizontal skylight to global horizontal photon flux ration includes a first quantum sensor pointed directly at the sun for measuring direct normal photon flux density in the wave band of about 0.4 to 0.7 μm and a second quantum sensor oriented horizontally for measuring global horizontal photon flux density in the range of about 0.4 to 0.7 μm.

20. The apparatus of claim 19, wherein said means for measuring and determining aerosol optical depth also includes a pressure-measuring means and microprocessor means programmed to calculate aerosol optical depth $\tau_a$ from the parameters including Rayleigh optical depth $\tau_R$, ambient pressure P, standard pressure at sea level $P_o$, ozone optical depth $T_o$, relative air mass $m_r$, an earth orbit eccentricity correction $\epsilon$, sunphotometer measurement of direct normal irradiance V, and an extraterrestrial direct normal irradiance value $V_o$ according to the formula $$\tau_a = \frac{-1}{m_r} \times \ln\left(\frac{\epsilon V}{V_o}\right) - \frac{P}{P_o}(\tau_R) - \tau_o.$$

21. Apparatus for correcting actual outdoor test performance output of a photovoltaic device to standard atmospheric optical condition output values on a real-time basis concurrently with the testing, comprising:

pressure measuring means for measuring ambient pressure at the test site;

first sunphotometer means to be located at the test site and pointed at the sun for measuring direct normal irradiation at a first wavelength;

second sunphotometer means to be located at the test site and pointed at the sun for measuring direct normal irradiation at a second wavelength;

third sunphotometer means to be located at the test site and pointed at the sun for measuring direct normal irradiation at a third wavelength;

fourth sunphotometer means to be located at the test site and pointed at the sun for measuring direct normal irradiation at a fourth wavelength;

first quantum sensor means to be located at the test site and pointed at the sun for measuring direct normal photon flux density in a first wave band;

second quantum sensor means to be located at the test site and oriented horizontally for measuring global horizontal photon flux density in said first wave band;

first pyranometer means to be located at the test site and pointed at the sun for measuring the direct normal irradiance in a second wave band;

second pyranometer means to be located at the test site and oriented horizontally for measuring the global horizontal irradiance in said second wave band;

first microprocessor means connected to said first, second, and third sunphotometer means and programmed for calculating aerosol optical depth for said first, second, and third wavelengths utilizing irradiance measurements for said first, second, and third wavelengths from said first, second, and third sunphotometer means, respectively;

second microprocessor means connected to said first and second quantum sensor means and to said first and second pyranometer means and programmed for calculating the ratio of diffuse horizontal skylight to global horizontal photon flux density from measurements by said first and second quantum sensor means and for calculating the ratio of diffuse irradiance to global horizontal irradiance form measurements by said first and second pyranometer means;

third microprocessor means connected to said third and fourth sunphotometer means and to said pressure measuring means and programmed for calculating precipitable water vapor utilizing measurements from said third and forth sunphotometer means and from said pressure measuring means;

fourth microprocessor means connected to said first, second, and third microprocessor means and programmed for generating a computer model of the solar spectrum;

fifth microprocessor means connected to said fourth microprocessor means for converting the computer solar spectrum model to a conversion model of irradiance on a surface tilted at an angular orientation to match the angular orientation of the photovoltaic device under test;

sixth microprocessor means connected to said fifth microprocessor means and to said photovoltaic device under test and programmed to generate a spectral-mismatch factor and for correcting actual performance responses of the photovoltaic device being tested to standard atmospheric optical condition performance responses.

22. The apparatus of claim 21, wherein said first, second, third, and fourth wavelengths are about 0.368 $\mu$m, 0.500 $\mu$m, 0.862 $\mu$m, and 0.940 $\mu$m, respectively, and said first and second wave bands are about 0.4 to 0.7 $\mu$m and about 0.3 to 1.1 $\mu$m, respectively.

* * * * *